United States Patent [19]

Soós et al.

[11] Patent Number: 4,521,612
[45] Date of Patent: Jun. 4, 1985

[54] PROCESS FOR THE SEPARATION OF ESTERS

[75] Inventors: Rudolf Soós; Rezso Kolta; Sándor Zoltán; Mária Tary, all of Budapest, Hungary

[73] Assignee: Chinoin Gyogyszer es Vegyeszeti Termekek Gyara Rt., Budapest, Hungary

[21] Appl. No.: 659,320

[22] Filed: Oct. 10, 1984

[30] Foreign Application Priority Data

Oct. 10, 1983 [HU] Hungary ............................... 3496/83

[51] Int. Cl.³ .......................................... C07C 69/743
[52] U.S. Cl. .................................................. 560/124
[58] Field of Search ........................................ 560/124

[56] References Cited

U.S. PATENT DOCUMENTS 4,250,326  2/1981  Fishman ............................. 560/124
4,288,610  9/1981  Rumonoski ........................ 560/124

*Primary Examiner*—Michael L. Shippen
*Attorney, Agent, or Firm*—Karl F. Ross; Herbert Dubno

[57] ABSTRACT

The present invention relates to a process for the selective separation of esters of the general formula II

A—COOR¹     II from mixtures containing the cyclopropane carboxylic acid esters of the general formula I

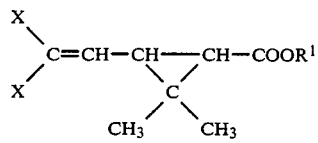

in addition to the said esters of the general formula II by reacting the said mixture with an amine of the general formula III

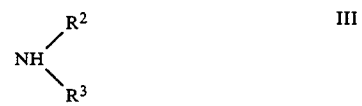

when removing the acid amides formed from the esters of the general formula II by washing the mixture with water of removing the esters of the general formula I by distillation.

The compounds of the general formula I are the intermediates of herbicides. The requested purity of the herbicides can be achieved if pure intermediates are used.

5 Claims, No Drawings

PROCESS FOR THE SEPARATION OF ESTERS

FIELD OF THE INVENTION

The present invention relates to a process for the selective separation of esters of the general formula II $$A-COOR^1 \qquad \text{II}$$

wherein

A stands for $-CH=CH-COOR^1$, $-CH_2OCH_2-COOR^1$, $-CH_2OCH[CH(CH_3)_2]-CH=CX_2$ or $-CH_2OCH[(CH_3)(CH_2X)]-CH=CX_2$, X is halogen, $R^1$ represents an alkyl group of 1 to 5 carbon atoms from mixtures containing the cyclopropane carboxylic acid esters of the formula I

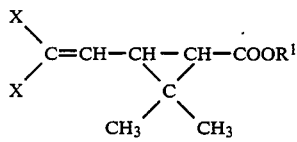

wherein $R^1$ and X are the same as set forth above, in addition to the said esters of formula II, by reacting the said mixture with an amine of the formula III

wherein $R^2$ stands for hydrogen, amino, oxy-alkyl of 2 to 5 carbon atoms or alkyl of 1 to 6 carbon atoms, $R^3$ represents hydrogen, oxyalkyl of 2 to 5 carbon or aminoalkyl of 1 to 5 carbon atoms or $R^2$ and $R^3$ represent together a $-CH_2CH_2OCH_2CH_2-$group, then removing the acid amides formed from the esters of the formula II by washing the mixture with water or removing the esters of the formula I by distillation.

In the formulae A, X, $R^1$, $R^2$, $R^3$ are always the same as defined hereinabove; therefore the definitions will not be repeated.

BACKGROUND OF THE INVENTION

The compounds of the formula I are the intermediates of pyrethroid type compounds with insecticidal action. The preparation of the active ingredients in the desired purity can only be carried out by using pure intermediates.

The compounds of the formula II are on one hand the characteristic by-products of the dienealkyldiazoacetate synthesis (Helv.Chim.Acta 7.390, 1924; J.Am.Chem.-Soc. 66.395, 1944; Coll.Czech.Chem. Commun. 24.2240, 1959) widely used for the preparation of cyclopropane carboxylic acids of the formula I, on the other hand they are formed from the impurities present in the 1,1-dihalo-4-methyl-1,3-pentadiene used for the synthesis.

The amount of the contaminating esters can reach even 15 to 20% of the target product of formula I depending on the conditions (the effectivity of the catalyst, temperature etc.) of the synthesis and the purity of the diene.

The separation of the esters of general formula I and II by distillation is very difficult as their vapor pressure are very close to each other; therefore the different compounds distillate together. The chromatographic method for their separation (Synthesis 1960, 600) is wearisome and expensive on an industrial scale therefore has not been widespread.

The purification of the synthesis product can be carried out by removing the alkali sensitive contaminations, e.g. maleinic acid and fumaric acid esters, from the contaminated intermediate product by saponifying the product by adding alkaline solutions and transforming the said contaminations to water soluble salts (Hungarian Patent Application No. CI-1983).

A similar procedure can also be used when alcoholic medium is applied. According to the procedure the alcoholic solution of the permethrinic acid ester previously purified by distillation is treated with aqeous alkaline solution (European Patent No. 0034875).

The technical application of these methods is very difficult. In the course of the procedures a solvent (water or alcohol) and an aqeous alkaline hydroxide solution of great volume are used. The aqeous alcoholic phase formed in the course of the latter procedure also contains the dissolved endproduct. The recovery of the endproduct and the regeneration of the solvent demand further technological steps.

OBJECTS OF THE INVENTION

We targeted our efforts to improve upon the purification of the reaction product of ethyldiazoacetate and 1,1-dichloro-4-methyl-1,3-pentadiene, i.e. to remove more by-products, to avoid the use of solvents and to provide a process being able to be used for any product of any phase even in continuous operation.

DETAILED DESCRIPTION OF THE INVENTION

The invention is based on the discovery that the ester by-products of the formula II of the permethrinic acid alkyl ester synthesis can be transformed into acid amides by the primary and secondary amines of the formula III even in anhydrous medium and without using a solvent, while the endproduct does not react with these compounds under the conditions of the procedure. The other valuable component, the 1,1-dichloro-4-methyl-1,3-pentadiene being present in the reaction mixture also does not suffer any damage.

The acid amides formed from the contaminating esters can be removed by a manner depending on the amine reagent used: if they are insoluble in the mixture they can be separated as a distinct phase or can be solved out by water. The derivatives possessing with a volatility significantly diverging from that of the target compound can be separated in pure form by distillation.

The procedure according to the invention can be used for the treatment of equally primary synthesis products (containing solvent, diene, target compound and synthesis by-products) and phase products obtained by distillation (containing regenerated diene and distillation fractions enriched in by-products) and for the purification of relatively pure target products containing only a few by-products. The procedure can be well adapted to the synthetic process and also permits of continuous operation.

If the procedure according to the invention is applied, the target product of the formula I and the diene do not suffer damages, while the compounds of the formula II are transformed into acid amides with great efficiency. The concentration of the latter compounds can be decreased even under 0.1%. The product treated can be separated by a simple manner into a target compound of the formula I of high purity and the diene being able to be recirculated to the synthesis mixture.

Several primary and secondary amines can be used as compounds of the formula III. The alkylamines, dialkylamines, alkyldiamines, mono and dialkanolamines having 2 to 6 carbon atoms in the alkyl moiety, morpholine and hydrazine react equally easily and quickly with the esters of the formula II. The mono- and dialkanol amines having 2 to 4 carbon atoms in the alkyl moiety are especially preferred.

The amines should be used in an amount of 100 to 120 mole % calculated for the amount equivalent with the esters of the formula II, but even a higher excess of the amines does not lead to undesirable side-reactions. The amine is chosen by taking into consideration technical points of view. The especially preferred mono- and dialkanol amines having 2 to 4 carbon atoms in the alkyl moiety can be dissolved in the mixture above all very poorly. Therefore the formation of acid amines is performed in heterogenous phase and the acid amides formed appear to be dissolved in the excess of the amine as a separate phase. If desired the separation can be eased by dissolving this phase in water or aqueous mineral acid solution.

In most cases the reaction can be performed spontaneously at room temperature if amines are used. As the esters of the formula I cannot react with amines even at a temperature of 80° C., the reaction can be completed within 30 to 60 minutes at a temperature of 50° to 60° C.

The formation of acid amides can be carried out with or without using a solvent. Alcohols of 1 to 4 carbon atoms, ketones, aliphatic and aromatic hydrocarbons may be used as solvent. The reaction can also be carried out in the presence of water.

The acid amides formed remain in the solution or separate in crystalline or liquid form as a distinct phase which phase can be separated by solving them out with water or diluted mineral acid, depending on the starting amine. If the acid amines remain dissolved in the solution, the mixture can be worked up by distillation.

The amine reagent may be introduced continuously or in one portion. When batch-type technology is used, it is preferred to charge the reagent in one portion thereafter to heat the mixture to 60° C. Under continuous operation both the addition of the amine reagent and the dissolution of the formed acid amide may be effected continuously.

The excess of the amine used for the reaction can be washed out by water or diluted aqueous mineral acid. These solvents also solve out the water soluble reaction products from the target product.

The raw synthesis mixture can also be effectively purified by the procedure according to the invention. The characteristic components of the said mixture are the diene used in an excess, the by-products of the formula II, unvolatile polymerized compounds, solvents (especially chlorinated hydrocarbons) and the catalyst of the synthesis (solved or unsolved copper compounds) in addition to the target product. The copper compounds form complex compounds with the amines and can also be solved out by water.

The esters of the formula I containing only a small amount of by-products of the general formula II concentrated by distillation may also be effectively purified. The concentration of the by-products can be reduced under 0.1 to 0.2% by treating with amines then washing with aqueous, diluted hydrochloric acid. Therefore the ester treated will becomes of high purity without any further distillation fractions.

SPECIFIC EXAMPLE

The invention is illustrated by the following, non-limiting examples.

EXAMPLE 1

To a flask of 250 ml volume, equipped with a stirrer 100 g of permethrinic acid ethyl ester distilled from the synthesis mixture and 9 g of enthanolamine are charged. The mixture is stirred at 60° C. for 60 minutes. The mixture of the acid amides formed separates as a distinct phase from the reaction mixture. To the whole mixture 80 ml of water are added thus the acid amides are dissolved. The mixture is cooled to 20° C. under stirring then the phases are separated after ceasing of the stirring. The organic (lower) phase (permethrinic acid ethyl ester) is washed with 30 ml of 2% by wight hydrochloric acid and dried over anhydrous sodium sulphate. The product is 87.6 g of permethrinic acid methyl ester.

The compositions of the starting material and the target product are as follows according to gas chromatographic analysis:

|  | starting material | | target product | |
|---|---|---|---|---|
|  | % | g | % | g |
| permethrinic acid ethyl ester | 87.4 | 87.4 | 98.8 | 96.52 |
| compound of the formula IV | 4.2 | 4.2 | 0.1 | 0.09 |
| compound of the formula V | 3.2 | 3.2 | 0.1 | 0.09 |
| compound of the formula VI | 2.4 | 2.4 | 0.1 | 0.09 |
| compound of the formula VII | 1.2 | 1.2 | 0.2 | 0.18 |
| compound of the formula VIII | 1.0 | 1.0 | 0.2 | 0.18 |
| other contaminants (total amount) | 0.6 | 0.6 | 0.5 | 0.45 |

IV.

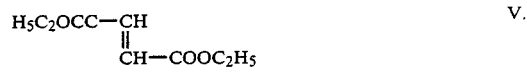

V.

VI.

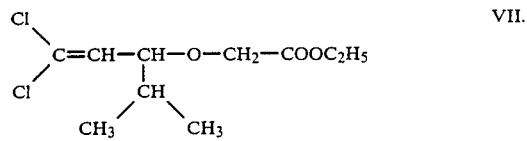

VII.

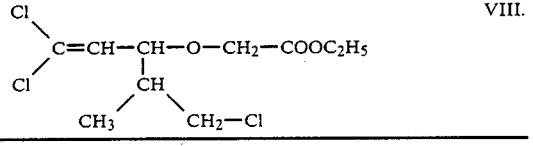

VIII.

The recovery of the permethrinic acid ethyl ester is 99%, the total amount of the esters being able to be transformed into acid amides (IV–VIII) is reduced from 12.0 g to 0.63 g.

EXAMPLE 2

The method of Example 1 is followed except that 7.5 g of hydrazine hydrate is used instead of ethanolamine.

The quality of the product and the yield are the same as in Example 1.

EXAMPLE 3

To a 250 ml flask equipped with a stirrer 100 g of permethrinic acid ethyl ester distilled from the synthesis mixture, having the same composition as the starting material of Example 1 and 10 g of butylamine are charged. The mixture is stirred at 60° C. for 60 minutes then distilled at a pressure of 1.3 kPa.

The yield of the distilled permethrinic acid ethyl ester is 84.0 g. its purity is 99.4%. The concentration of any of the contaminating compounds does not exceed 0.1%.

The recovery of the permethrinic acid ethyl ester is 95%.

EXAMPLE 4

The procedure of Example 1 is followed except that 100 g of permethrinic acid ethyl ester predistillate and 30 g of diethanolamine are used. 76.7 g of product are obtained.

The compositions of the starting material and the product are as follows:

|  | starting material | | target product | |
| --- | --- | --- | --- | --- |
|  | % | g | % | g |
| dichloromethyl pentadiene | 25.4 | 25.4 | 32.3 | 24.77 |
| permethrinic acid ethyl ester | 50.2 | 50.2 | 63.6 | 48.78 |
| compound of the formula IV | 10.5 | 10.5 | 0.3 | 0.23 |
| compound of the formula V | 8.0 | 8.0 | 0.3 | 0.23 |
| compound of the formula VI | 1.5 | 1.5 | 0.05 | 0 |
| compound of the formula VII | 0.8 | 0.8 | 0.1 | 0.08 |
| compound of the formula VIII | 0.6 | 0.6 | 0.1 | 0.08 |
| other contaminants (total amount) | 3.0 | 3.0 | 3.3 | 2.53 |

The recovery of permethrinic acid ethyl ester is 97.2% while that of the dichloromethyl pentadiene is 97.5%. The amount of the contaminating ester is reduced from 21.4 g to 0.62 g.

EXAMPLE 5

One proceeds as described in Example 3 except that 100 g of 1,1-dichloro-4-methyl-1,3-pentadiene regenerated from the synthesis mixture and 20 g of morpholine are used for the experiment. After the treatment the product is distilled at a pressure of 5.0 kPa.

The compositions of the starting material and the target product are as follows:

|  | starting material | | target product | |
| --- | --- | --- | --- | --- |
|  | % | g | % | g |
| 1,1-dichloro-4-methyl-1,3-pentadiene | 78.0 | 78.0 | 90.3 | 74.14 |
| permethrinic acid ethyl ester | 5.0 | 5.0 | 5.7 | 4.68 |
| compound of the formula IV | 7.0 | 7.0 | 0.2 | 0.16 |
| compound of the formula V | 6.0 | 6.0 | 0.3 | 0.23 |
| other contaminations | 4.0 | 4.0 | 3.5 | 2.87 |

In the product 95.0% of the 1,1-dichloro-4-methyl-1,3-pentadiene and 93.6% of the permethrinic acid ethyl ester are recovered. 96.7% of the contaminating esters and 28.2% of the other, unidentified contaminations could be eliminated.

The distillate can be used for the synthesis without any further purification.

EXAMPLE 6

To a 1 liter flask equipped with a stirrer 600 g of raw synthesis mixture of permethrinic acid ethyl ester and 36 g of ethylene diamine are charged. The mixture is stirred for 1 hour at a temperature of 60° C. then the stirring is continued for further 15 minutes after the addition of 200 ml of water. On ceasing the stirring the solution is cooled to 20° C. and the phases are separated. The organic phase is washed with 200 ml of 2% by weight hydrochloric acid. The weight of the organic phase is 540 g.

The compositions of the starting material and the target product are as follows:

|  | starting material | | target product | |
| --- | --- | --- | --- | --- |
|  | % | g | % | g |
| dichloroethane | 30.0 | 180.0 | 30.0 | 162.0 |
| dichloromethyl pentadiene | 48.0 | 288.0 | 51.7 | 279.0 |
| permethrinic acid ethyl ester | 15.0 | 90.0 | 16.3 | 88.0 |
| compound of the formula IV | 1.1 | 6.6 | 0 | 0 |
| compound of the formula V | 0.8 | 4.8 | 0.1 | 0.5 |
| compound of the formula VI | 0.7 | 4.2 | 0 | 0 |
| compound of the formula VII | 0.2 | 1.2 | 0.1 | 0.5 |
| compound of the formula VIII | 0.2 | 1.2 | 0.1 | 0.1 |
| other volatile components | 0.5 | 3.0 | 0.2 | 1.6 |
| distillation residue | 3.5 | 21.0 | 1.4 | 7.7 |

As a result of the treatment 96% of the esters of the formula IV to VIII and 63% of the distillation residue could be eliminated. By simple distillation ot the product, permethrinic acid ethyl ester of higher purity than 96% and dichloroethane and 1,-dichloro-4-methyl-1,3-pentadiene usable for the synthesis without further distillation can be obtained.

EXAMPLE 7

The procedure of Example 6 is followed except that 42 g of diethylamine are used instead of ethylene diamine. The yield and the composition of the product are the same as obtained in Example 6.

What we claim is:

1. Process for the selective separation of an ester of the formula II $$A-COOR^1 \qquad II$$

wherein

A stands for $-CH=CH-COOR^1$, $-CH_2OCH_2COOR^1$, $-CH_2OCH[CH(CH_3)_2]-CH=CX_2$ or $-CH_2OCH[CH(CH_3)(CH_2X)]-CH=CX_2$ X is halogen, $R^1$ represents an alkyl group of 1 to 5 carbon atoms, from mixtures containing the cyclopropane carboxylic acid esters of the formula I

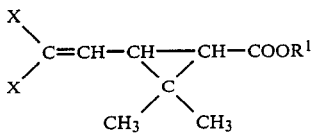

in addition to the said esters of the formula II which comprises reacting the said mixture with an amine of the formula III

wherein $R^2$ stands for hydrogen, amino, oxyalkyl of 2 to 5 carbon atoms, or aminoalkyl of 2 to 5 carbon atoms or alkyl of 1 to 6 carbon atoms, $R^3$ represents hydrogen oxyalkyl of 2 to 5 carbon atoms or aminoalkyl of 1 to 5 carbon atoms or $R^2$ and $R^3$ together represent a —$CH_2CH_2OCH_2CH_2$— group, then removing the acid amides formed from the esters of the formula II by washing the mixture with water or removing the esters of the formula I by distillation.

2. A process as claimed in claim 1 which comprises using the amine of the formula III in the amidating reaction in an amount of 105 to 120 mole % calculated for the esters of the formula II.

3. A process as claimed in claim 1 which comprises using a monoalkanolamine having 2 to 4 carbon atoms in the amidating reaction.

4. A process as claimed in claim 1 which comprises carrying out the amidation reaction at a temperature of 20° to 80° C. within 10 to 120 minutes.

5. A process as claimed in claim 1 which comprises carrying out the amidating reaction in the presence of a chlorinated aliphatic hydrocarbon and/or aromatic hydrocarbon solvent.

* * * * *